United States Patent
Derevyagin et al.

(10) Patent No.: US 7,350,970 B2
(45) Date of Patent: Apr. 1, 2008

(54) DEW POINT MEASUREMENT METHOD AND DEVICE FOR CARRYING OUT SAID METHOD

(75) Inventors: Alexandr Mikhailovich Derevyagin, Sivtsev Vrazhek per., 44-23, Moscow 119002 (RU); Alexander Sergeevich Fomin, St. Petersburg (RU); Sergei Viktorovich Seleznev, Saratov (RU)

(73) Assignee: Alexandr Mikhailovich Derevyagin, Moscow (RU)

( * ) Notice: Subject to any disclaimer, the term of this patent is extended or adjusted under 35 U.S.C. 154(b) by 4 days.

(21) Appl. No.: 10/528,331

(22) PCT Filed: May 25, 2004

(86) PCT No.: PCT/RU2004/000197

§ 371 (c)(1),
(2), (4) Date: Mar. 18, 2005

(87) PCT Pub. No.: WO2004/106898

PCT Pub. Date: Dec. 9, 2004

(65) Prior Publication Data

US 2006/0083287 A1    Apr. 20, 2006

(30) Foreign Application Priority Data

May 30, 2003    (RU)    ................... 2003116084

(51) Int. Cl.
*G01N 25/02*    (2006.01)
(52) U.S. Cl. .................. 374/28; 374/19; 73/29.02
(58) Field of Classification Search ................. 374/17, 374/18, 19, 20, 27, 28
See application file for complete search history.

(56) References Cited

U.S. PATENT DOCUMENTS

| 4,652,745 | A | | 3/1987 | Zanardelli |
| 4,701,052 | A | * | 10/1987 | Schoen, Jr. ............. 356/369 |
| 5,022,045 | A | * | 6/1991 | Elliott .................. 374/20 |
| 5,052,818 | A | * | 10/1991 | Nishizawa et al. ...... 374/17 |
| 5,249,856 | A | * | 10/1993 | Dreier ................. 312/238 |
| 5,804,817 | A | | 9/1998 | Seiler et al. |
| 6,174,081 | B1 | * | 1/2001 | Holm .................. 374/161 |

FOREIGN PATENT DOCUMENTS

| JP | 57064130 A | * | 4/1982 |
| RU | 2 085 925 C1 | | 7/1997 |

OTHER PUBLICATIONS

Fink et al, "A Dielectric Omnidirectional Reflector", Nov. 27, 1998, Science, New Series, vol. 282, No. 5394, pp. 1679-1682.*
English Abstract of 2 085 925 C1 Published Jul. 27, 1997.

* cited by examiner

Primary Examiner—Gail Verbitsky
Assistant Examiner—Mirellys Jagan
(74) Attorney, Agent, or Firm—Ladas & Parry LLP

(57) ABSTRACT

The invention relates to measuring engineering. In order to increase accuracy by increasing sensitivity, for the inventive dew point measurement method a light flux polarized in the plane of incidence thereof is used and directed towards the condensation surface of a dielectric cooled element at an angle at which the light flux is not reflected from the condensation surface of the cooled element in the absence of condensate.

9 Claims, 1 Drawing Sheet

DEW POINT MEASUREMENT METHOD AND DEVICE FOR CARRYING OUT SAID METHOD

FIELD OF THE INVENTION

The invention relates to a field of measuring engineering, and in particular, to a measurement of humidity of gases by a technique of a dew point, and may be used in dew-point hygrometers, indicators of a corroding condensate, as well as in aims of research for determination of a concentration value of condensed admixtures in a predetermined volume of gas to be studied and a temperature of hydrate formation in a gas etc.

PRIOR ART

It is known a method for dew point measurement comprising feeding gas to be studied onto a cooled portion of an optically transparent body through which is directed a light flux, and registering a change of a light flux intensity, advent of the dew point being determined on the basis of the registered change, as well as a device for dew point measurement implemented in a given method, the device comprising the cooled portion of the optically transparent body, the portion is included in a housing and connected through light guides with radiators and a light flux transducer being connected to a register, the device comprising also a cooler and a temperature sensor (see SU patent No. 1744618, Int. Cl. G01N 25/66, published Jun. 30, 1992).

The drawback of the known technical solutions is a low reliability because of possible pollutions with admixtures of gas to be studied of the optically transparent body because of which arise a unnecessary layer which may bring to inaccurate measurements and a loss of efficiency in operation.

The method to be closest to the proposed one by a technical essence is a method for dew point measurement, comprising feeding gas to be studied onto a cooled element with a condensation surface onto which a light flux is directed and registering the value of the light flux reflected from the condensation surface, advent of the dew point being determined on the basis of the registered value (see the RF patent No. 22085925, Int. Cl. G01N 25/08, published Jul. 20, 1995).

The drawback of the known method is a relatively low accuracy of measurement caused by a presence of a relatively long transient process when measuring.

The device to be closest to the proposed one by a technical essence is a device for dew point measurement, comprising a cooled element contained in a housing equipped with a sampling tube, the cooled element is provided with a condensation surface and is connected through an optical element to a radiator, the proposed device comprises further a register, a cooler and a temperature sensor (see the RF patent No. 22085925, Int. Cl. G01N 25/08, published Jul. 20, 1995).

The drawback of the known device is a relatively low sensitivity which decreases the accuracy of measurement since the transient process when fixing the dew point is relatively long.

Functionalities of the known device are limited, moreover, only by its basic purpose—by the measurement of the dew point.

DISCLOSURE OF THE INVENTION

In base of the invention is stated a task of increasing the accuracy of measurement owing to increasing the sensitivity.

An additional technical task is widening of functionalities owing to providing a measurement of a concentration value of condensed admixtures in a predetermined volume of the studied gas during a certain period of time, as well as owing to a reliable registration of water drops or hydrates and a possibility of autocalibration.

This task is solved by the fact that in a method for dew point measurement, comprising feeding gas to be studied onto a cooled element with a condensation surface onto which a light flux is directed and registering the value of the light flux reflected from the condensation surface, advent of the dew point being determined on the basis of the registered value, a light flux polarized in a plane of its incidence is used, and the angle at which it is directed onto the condensation surface of the cooled element is selected so that there is no reflection of the light flux in the absence of a condensate from the condensation surface of the cooled element, which is made of a dielectric, besides, a phase difference between beams reflected from the condensation surface of the cooled element and from the surface of a condensate film is additionally measured, thickness h of the condensate film on the condensation surface of the cooled element is determined, and the concentration of condensed admixtures in a predetermined volume of the studied gas is determined on the basis of the value of the thickness of the film formed during a certain period of time.

In accordance with another invention, in a device for dew point measurement comprising a cooled element contained in a housing equipped with a sampling tube, the cooled element is provided with a condensation surface and is connected through an optical element to a radiator, a register, a cooler a temperature sensor, the cooled element provided with a condensation surface is made in the form of a dielectric plate, the radiator—in the form of a source of light polarized in the plane of incidence thereof, wherein the optical element is positioned in such a manner that the light flux of the source of polarized light is directed onto the condensation surface of the cooled element, preferably at an angle, the tangent of which is equal to the refraction index—Bruster angle, herewith the direction of the polarized light flux onto the condensation surface of the cooled element is selected at an angle within the range of ±9° of the value of the Bruster angle, besides, the device is provided with at least one additional register serving for measurement of scattered beams reflected from the surface of the formed condensate, wherein the housing is equipped with a cooler and a temperature sensor which are mounted on the sampling tube thereof.

The essence of the invention is that a usage of the light flux being polarized in the plane of its incidence and directed at Bruster angle onto the dielectric surface of the cooled element allows to provide a substantial increase of the sensitivity to an appearance of condensed admixtures that increases the accuracy of the dew point measurement. Besides, appear additional opportunities to study the gas, to autocalibrate the device that widens functionalities of the device.

BEST VARIANT OF THE EMBODIMENT OF THE INVENTION

Figure 1:
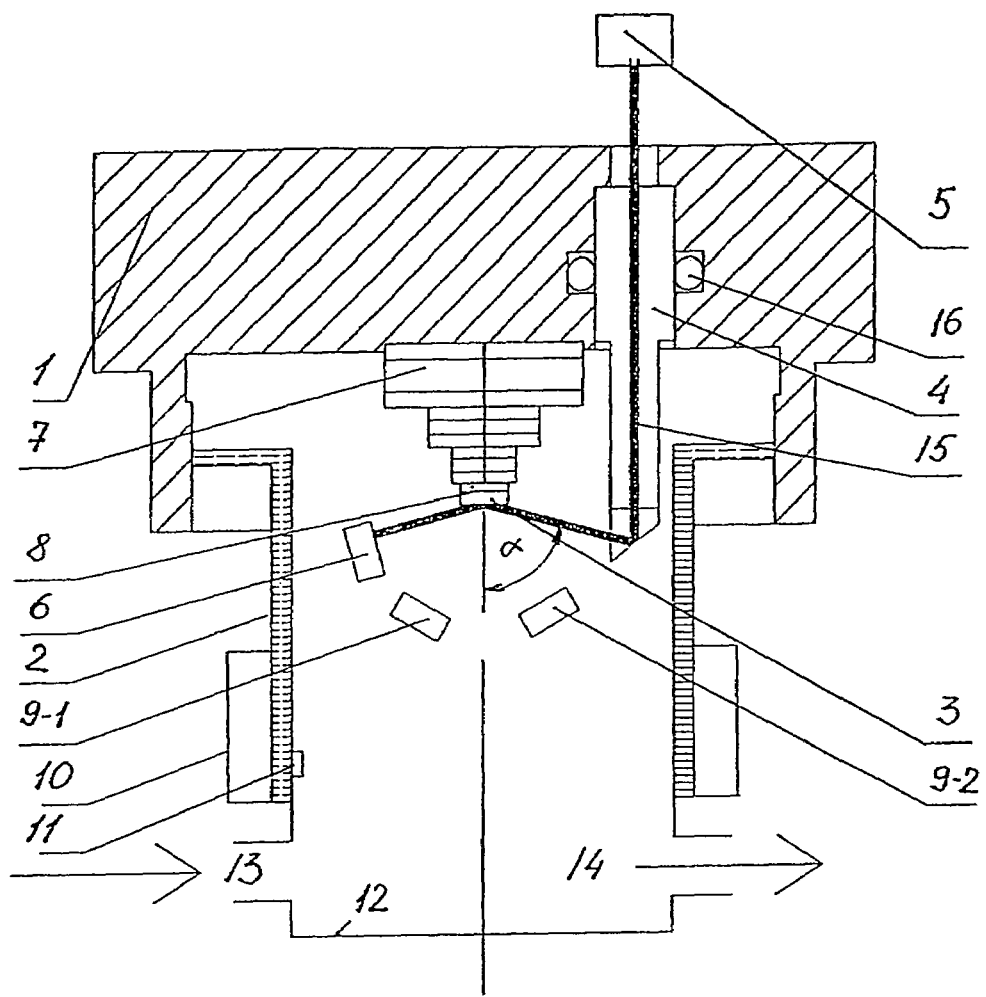
FIG. 1 illustrates a structure of the claimed device.

A method for dew point measurement is in feeding gas to be studied onto a cooled element with a condensation surface onto which a light flux is directed and in registering the value of the light flux reflected from the condensation surface, advent of the dew point being determined on the basis of the registered value.

A peculiarity of the invention is that a light flux polarized in a plane of its incidence is used and it is directed onto the condensation surface of the cooled element at an angle at which one is no reflection of the light flux from the condensation surface of the cooled element which is made of a dielectric.

It should be noted that in accordance with Bruster law if the light flux falls onto the surface of a dielectric at the angle α the tangent of which is equal to the refraction index then the light reflected from the surface of the dielectric is fully polarized (see www.RUBRICON.ru., Russian Encyclopaedia).

Therefore when falling the light, being polarized parallel to a plane of incidence (p-component), onto a dielectric surface in the absence of a condensate no reflection takes place from the polarized beams being fed onto this surface since they are refracted into a reflecting medium i.e. are absorbed in a dielectric (see Appendix: B.S.E.(Big Soviet Encyclopaedia), Mirror reflection of light,). And when appearing a condensate a part of light polarized flux does not reach a dielectric, and instantly takes place a reflection of the polarized beams and a reflected light flux is fixed by register.

For determining a value of concentration of the condensed admixtures in a predetermined volume of the studied gas the phase difference between beams reflected from the condensation surface of the cooled element and from the surface of a condensate film is measured, and thickness h of the condensate film, for example, of heavy hydrocarbons or spirit on the condensation surface of the cooled element is calculated in accordance with the formula:

$$h = \frac{(\varphi - \pi) \cdot \lambda}{2\pi \cdot 2 \cdot n_1 \cdot \text{Sin}\alpha \left( \frac{1}{\text{Sin}\beta \cdot \text{Cos}\beta} - tg\beta \right)},$$

where φ—the phase difference between beams,
λ—the wavelength in vacuum,
$n_1$—the refraction index of gas to be studied,
α—Bruster angle,
β the angle of the refraction of a beam in the condensate film.

After that on the basis of the thickness of the film being formed during a certain period of time the concentration of the condensed admixtures is determined.

The device for dew point measurement which realizes the claimed method comprises a housing 1 equipped with sampling tube 2, the housing 1 contains a cooled element 3 provided with a condensation surface and connected through an optical element 4 to a radiator 5. Besides, the device further contains a register 6, a cooler 7 and a temperature sensor 8.

A peculiarity of the invention is that the cooled element 3 provided with the condensation surface is made in the form of a dielectric plate, the radiator 5—in the form of a source of light polarized in the plane of incidence thereof.

Herewith the optical element 4 is positioned in such a manner that the light flux of the source of polarized light is directed onto the condensation surface of the cooled element 3, preferably at an angle, the tangent of which is equal to the refraction index (see the Bruster angle, Russian Encyclopaedia).

The selection of this angle is made within the range ±9° of the value of Bruster angle.

The indicated range is selected on the basis of experimental tests.

Besides, the device is provided with at least one additional register 9-1 serving for registration of water, as well as with a second additional register 9-2 serving for registration of ice which are formed on the condensation surface of the cooled element 3.

It should be noted that the housing 1 is equipped with a cooler 10 and a temperature sensor 11.

A positioning of registers 9-1 and 9-2 is selected experimentally. The sampling tube 2 has a bottom 12, inlet and outlet holes 13 and 14 accordingly. This provides a fixation of a predetermined volume of the studied gas.

An optical element 4 through which passes a light flux 15 is hermetically sealed with help of a packing ring 16.

The Device Operates in the Following Manner

When positioning the device into the medium of the gas to be studied or an admixture of gases the last goes onto the condensate surface of the cooled element 3, and in case of absence in it of condensate admixtures the condensate is not deposited and the polarized light flux being directed at Bruster angle is not reflected from the surface of the dielectric since it is absorbed in it.

The register 6 does not fix the light beams therefore and does not take place a registration of the dew point temperature.

In the presence of condensed admixtures in the gas to be studied on the condensation surface of the cooled element 3 at a definite temperature are formed a layer of the condensate and/or small dispersion drops of ball-shaped form or crystals of hoar-frost or hydrates.

Owing to the reflection of the light flux from the surface of condensate at a definite temperature of the cooled element 3 takes place an operation of the register 6.

It should be noted herewith that the registration of the light flux takes place even at an insignificant appearance of the condensate on the condensation surface of the cooled element 3. This defines the high sensitivity of the device and therefore the accuracy of the measurement.

Figure 2:
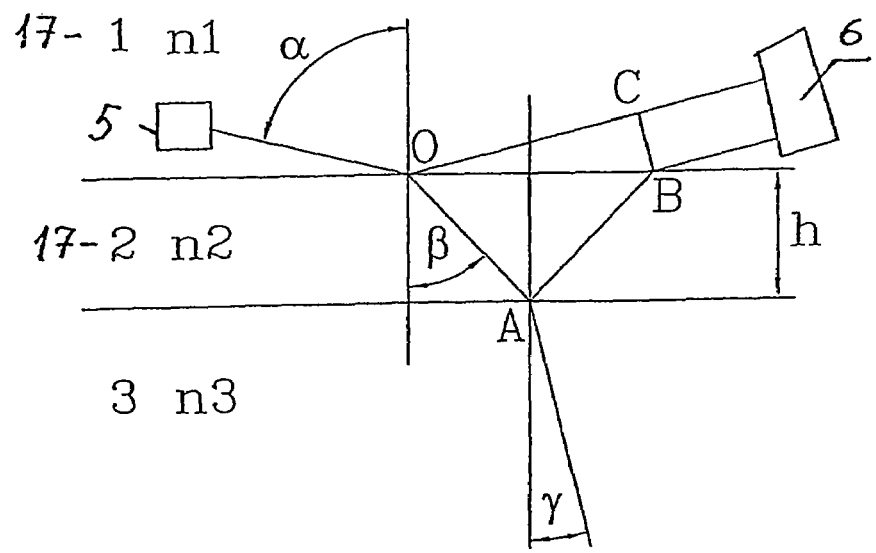
FIG. 2 shows a diagram elucidating a principle of measurement of an increment of thickness of the deposited film.

The proposed device allows to determine the value of the concentration of condensed admixtures in a predetermined volume of the studied gas owing to the measurement of the increment of a thickness of the deposited film (see FIG. 2).

In this case a reference number 17-1 nominates gas to be studied which has the refraction index $n_1$, 17-2 nominates a deposited film having the thickness h and the refraction index $n_2$, and a 3—the cooled element made of dielectric having the refraction index $n_3$.

This structure is illuminated with the light source being polarized parallel to the plane of its incidence at the angle α—Bruster angle. On two interfaces take place reflections.

An analysis shows that when $$\alpha = arctg\ (n_3/n_1) \qquad (1)$$

the coefficients of reflection from both interfaces are equal in magnitude and are opposite in phase.

The phase difference φ between beams passing to the register along the trajectories OAB and OC is determined in accordance to the following expression:

$$\varphi = \frac{2\pi}{\lambda} \cdot 2 \cdot h \cdot n_1 \cdot \sin\alpha \cdot \left(\frac{1}{\sin\beta \cdot \cos\beta} - tg\beta\right) + \pi, \quad (2)$$

where λ—the wavelength in vacuum.

It is clear that the phase difference φ—the periodic function of thickness h of the film, therefore when the interference of beams reflected from to interfaces takes place the intensity of the light coming to a photodetector of light will be also the periodic function of h. By means of calculation of periods of changing the intensity of the light is determined the increment of thickness of the film—h.

The condition (1) corresponds to Bruster angle for the interface "gas-substrate" i.e. for the thickness of the film being equal to zero. At small deviations from the condition (1) the described effect does not disappear in the range ±9°, however the amplitude of modulation of the intensity of the light is decreased due to a violation of equality of coefficients of reflection.

After that may be determined the thickness h of the condensate film in a accordance with the formula:

$$h = \frac{(\varphi - \pi) \cdot \lambda}{2\pi \cdot 2 \cdot n_1 \cdot \sin\alpha \left(\frac{1}{\sin\beta \cdot \cos\beta} - tg\beta\right)}, \quad (3)$$

where φ—the phase difference between beams,
λ—the wavelength in vacuum,
$n_1$—the refraction index of gas to be studied,
α—Bruster angle,
the angle of the refraction of a beam in the condensate film. After some conversions may be obtained the following:

$$h = (\varphi - \pi)\frac{\lambda \cdot tg\beta}{4\pi \cdot n_1 \cdot \sin\alpha}. \quad (4)$$

When using the refraction law may be obtained the most convenient formula for the calculation of the thickness h of the film:

$$h = (\varphi - \pi)\frac{\lambda \cdot tg\left(\text{ArcSin}\left(\frac{n_1 \cdot \sin\alpha}{n_2}\right)\right)}{4\pi \cdot n_1 \cdot \sin\alpha}, \quad (5)$$

The additional registers 9-1 and 9-2 are used for fixing the appearance of small dispersion drops of ball-shaped form and crystals of hoar-frost or hydrates accordingly. Herewith their positioning is determined by experiment.

The cooler 10 and the temperature sensor 11 are used for preliminary cooling of the gas positioned in the sampling tube 2. Herewith the dew point temperature in the volume of the tube 2 becomes equal to the temperature of the tube 2. Therefore the dew point temperature at the meter indirectly corresponds to the same temperature that may be used when autocalibrating the device.

The shape of the optical element 4 may be different one. The chief main think is the direction of the light flux 15.

Thus, in the proposed technical solutions is achieved the stated technical result—increasing the accuracy of measurement at the widening of functionalities.

INDUSTRIAL APPLICABILITY

The described advantages of the proposed technical solutions ensure them the possibility of wide industrial usage in the field of the measuring engineering for the measurement of humidity of gases by a method for dew point measurement and may be used in dew-point hygrometers, indicators of corroding condensate, as well as in aims of research for determination of a concentration value of condensed admixtures in a predetermined volume of a gas to be studied and a temperature of a hydrate formation in a gas etc.

The invention claimed is:

1. A method for dew point measurement, comprising the steps of:
   providing cooled element having a condensation surface on a dielectric plate;
   feeding a gas to be studied onto the with a condensation surface to form a condensate film on the condensation surface onto which a light flux is incident;
   measuring the dew point from a value of reflection of the light flux from the condensation surface,
   polarizing the incident light flux in a plane of incidence,
   selecting an angle for the incident light flux so that there is no reflection of the incident light flux in the absence of the condensate film on the condensation surface;
   measuring a phase difference between the light flux reflected from the condensation surface of the cooled element and from the surface of the condensate film;
   determining a thickness of the condensate film on the condensation surface of the cooled element;
   determining a concentration of condensed admixtures in a predetermined volume of the gas on the basis of the value of the thickness of the film formed during a certain period of time.

2. A device for dew point measurement, comprising a housing equipped with a sampling tube, the housing containing a cooled element having a condensation surface and connected through an optical element to a radiator, the housing further containing a register, cooler and temperature sensor, the improvements wherein
   the cooled element has a condensation surface dielectric plate,
   the radiator is a source of light polarized in a plane of incidence on the condensation surface at an angle about equal to the Bruster angle of the condensation surface, and
   the register includes means for determining the following:
   (a) a phase difference between light reflected from the condensation surface of the cooled element and from the surface of a condensate film that may form on the condensation surface;
   (b) a thickness of the condensate film on the condensation surface of the cooled element; and
   (c) a concentration of condensed admixtures in a predetermined volume of a gas fed onto the condensation surface on the basis of the value of the thickness of the film formed during a certain period of time.

3. The device according to claim 2, wherein the angle is within the range of ±90° of the Bruster angle.

4. The device according to claim 2, further comprising at least one additional register for measuring scattered light reflected from the surface of the condensate film that may form on the condensation surface.

5. The device according to claim 2, wherein the cooler and temperature sensor are mounted on the sampling tube.

6. A method for dew point measurement, comprising feeding gas to be studied onto a dielectric cooled element having a condensation surface onto which a light flux is directed and registering the value of the light flux reflected from the condensation surface, advent of the dew point being determined on the basis of the registered value, wherein the light flux is polarized in a plane of its incidence, and the angle at which it is directed onto the condensation surface of the cooled element is selected so that there is no reflection of the light flux in the absence of a condensate from the condensation surface of the cooled element; a phase difference between light flux reflected from the condensation surface of the cooled element and from a surface of a condensate film that may form on the condensation surface and is measured; a thickness of the condensate film is determined, and the concentration of condensed admixtures in a predetermined volume of the studied gas is determined on the basis of the value of the thickness of the film formed during a certain period of time.

7. A device for measuring a dew point of a gas, comprising a housing equipped with a sampling tube, the housing containing a dialectric cooled element provided with a condensation surface and connected through an optical element to a radiator, wherein the dielectric cooled element is provided on a dielectric plate on which a condensate film may be formed, the radiator is a source of light polarized in the plane of incidence thereof, wherein the optical element is positioned such that the light flux of the source of polarized light is directed onto the condensation surface of the cooled element, at an angle within the range of ±9° of the value of the Bruster angle, the housing further containing a register made capable to measure a phase difference between the light flux reflected from the condensation surface of the cooled element and from a surface of the condensate film such that the register calculates:

(a) a thickness of the condensate film; and (b) a concentration of condensed admixtures in a predetermined volume of the gas on the basis of the value of the thickness of the film formed during a certain period of time.

8. The device according to claim 7, further comprising at least one additional register for measuring scattered light flux reflected from the surface of the condensate film.

9. The device according to claim 7, wherein the housing is equipped with a cooler and a temperature sensor, which are mounted on the sampling tube thereof.

* * * * *